(12) United States Patent  (10) Patent No.: US 9,839,551 B2
Garth et al.  (45) Date of Patent: Dec. 12, 2017

(54) PNEUMATIC ORTHOSIS

(71) Applicant: Aspen Medical Partners, LLC, Irvine, CA (US)

(72) Inventors: Geoffrey Garth, Long Beach, CA (US); Steven Burke, Huntington Beach, CA (US)

(73) Assignee: ASPEN MEDICAL PARTNERS, LLC, Irvine, CA (US)

( * ) Notice: Subject to any disclaimer, the term of this patent is extended or adjusted under 35 U.S.C. 154(b) by 276 days.

(21) Appl. No.: 14/607,840

(22) Filed: Jan. 28, 2015

(65) Prior Publication Data

US 2016/0213503 A1 Jul. 28, 2016

(51) Int. Cl.
*A61F 5/01* (2006.01)
*A61F 5/055* (2006.01)

(52) U.S. Cl.
CPC .............. *A61F 5/012* (2013.01); *A61F 5/055* (2013.01)

(58) Field of Classification Search
CPC ...... A61F 5/055; A61F 5/05883; A61F 5/012; A61F 5/34; A61F 5/028; A61F 5/05816; A42B 3/0473; A61H 9/0078
See application file for complete search history.

(56) References Cited

U.S. PATENT DOCUMENTS

| | | |
|---|---|---|
| 3,164,151 A | 1/1965 | Nicoll |
| 4,401,111 A | 8/1983 | Blackstone |
| 4,543,947 A | 10/1985 | Blackstone |
| 4,732,144 A | 3/1988 | Cunanan |
| 4,993,409 A | 2/1991 | Grim |
| 5,403,266 A * | 4/1995 | Bragg ................ A61F 5/055 602/13 |
| 5,415,624 A * | 5/1995 | Williams ............ A61F 5/0104 602/14 |
| 6,210,354 B1 | 4/2001 | Ousdal |
| 6,500,136 B2 | 12/2002 | Meyer |
| 6,637,059 B1 | 10/2003 | Baker |
| 6,896,662 B2 | 5/2005 | Heffez |
| 6,936,002 B2 | 8/2005 | Kochamba et al. |
| 7,468,048 B2 * | 12/2008 | Meehan ............... A61F 5/0104 602/13 |
| 8,038,635 B2 | 10/2011 | Dellanno |
| 8,920,351 B2 * | 12/2014 | Polliack ............. A61F 5/05825 128/96.1 |
| 2006/0135897 A1 | 6/2006 | Dellanno |
| 2011/0172579 A1 | 7/2011 | Chiu |
| 2012/0291189 A1 | 11/2012 | Chambers |
| 2014/0130261 A1* | 5/2014 | Gumbrecht ........... A47C 7/383 5/644 |
| 2014/0330184 A1 | 11/2014 | Kilbey |
| 2015/0190266 A1 | 7/2015 | Hollern |

FOREIGN PATENT DOCUMENTS

JP  EP 0934732 A2 *  8/1999  ........... A41H 37/001

* cited by examiner

*Primary Examiner* — Ophelia A Hawthorne
(74) *Attorney, Agent, or Firm* — Fish IP Law, LLP

(57) ABSTRACT

An adjustable support for a pneumatic orthosis is provided. The adjustable support includes an inflatable member and a pod that acts diffuse, concentrate, localize or otherwise direct a force applied to a wearer's body via the inflatable member. Contemplated adjustable supports can be adjustably coupled to any suitable brace panel such that the apex of the inflatable member is movable relative to a midpoint of the panel of the brace as desired.

20 Claims, 5 Drawing Sheets

PNEUMATIC ORTHOSIS

FIELD OF THE INVENTION

The field of the invention is pneumatic orthosis.

BACKGROUND

The background description includes information that may be useful in understanding the present invention. It is not an admission that any of the information provided herein is prior art or relevant to the presently claimed invention, or that any publication specifically or implicitly referenced is prior art.

Efforts have been made to develop alternatives to traditional orthotic devices, which tend to be uncomfortable and suitable only for specific persons or have limited uses. For example, U.S. Pat. No. 8,038,635 to Dellano teaches a forward head positioning corrective collar including an inflatable assembly. Dellano's inflatable assembly includes multiple inflatable units, each of which can be independently inflated by coupling a tube and bulb to the selected inflatable unit to target a specific vertebra.

Unfortunately, Dellano's collar suffers numerous disadvantages. For example, the pressure of the Dellano collar's inflatable member cannot readily be adjusted by a user while wearing the brace, the inflatable assembly is not suitable for use in any other orthotic device, and each inflatable unit is apparently independently inflated.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Some prior attempts to provide pneumatic solutions to overcome one or more of the disadvantages of traditional orthotic devices are disclosed in U.S. Pat. No. 3,164,151 to Nicoll, U.S. Pat. No. 4,401,111 to Blackstone, U.S. Pat. No. 4,732,144 to Cunanan, U.S. Pat. No. 6,896,662 to Heffez, and U.S. Pat. No. 6,936,002 to Kochamba. Unfortunately, these attempts each suffer from one or more similar disadvantages, including for example, a lack of ability to adjust a positioning of an apex of the inflatable member, and difficulty of use.

Thus, there is still a need for improved pneumatic orthosis.

SUMMARY OF THE INVENTION

The inventive subject matter provides apparatus, systems and methods in which an adjustable support for pneumatic orthosis includes a pad coupled to an inflatable member and a pod. The inflatable member can be inflated using at least one of a pump and a tube coupled to the member, and can thereby provide an inward force or pressure to a portion of a wearer's body. The pod can be positioned relative to the inflatable member (e.g., between an inflatable member and an outer material of the pad, between an inflatable member and a neck of a wearer, or any other position at least partially between the inflatable member and neck of a wearer) such that the inward force is concentrated, diffused, or otherwise adjusted or directed.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some aspects of the inventive subject matter, the adjustable support can be adjustably coupled to one or more panels of various orthotic devices, for example, =an inner surface of a cervical collar's panel. In some preferred embodiments, a placement of the central point (apex) of the adjustable support's pad, pod or inflatable member relative to the panel could be adjusted. In these and some other contemplated embodiments, it can be advantageous to provide a pad that is oversized relative to the panel along one, two, three or even more dimensions since the pad (and adjustable support) will typically be made of a softer material than the panel. The pad could have one or more of a length, a width, a height, a depth, and a surface area that is greater than that of the panel to which it can adjustably couple.

Stated simply, the pad is preferably larger than the panel to ensure the panel is sufficiently covered at all times, even when the center portion of the pad is adjusted relative to the panel. Viewed from another perspective, the adjustable member having an oversized pad can be attached to a panel at different positions without causing the panel itself to contact a neck of the wearer and cause discomfort. This allows a user to attach the adjustable support to a panel in a manner such that a customized force can be applied to a specified portion of the wearer's body without exposing a wearer's skin to the panel's inner surface.

Additionally or alternatively, it is contemplated that an adjustable support of the inventive subject matter could be sized and dimensioned to couple to an inner surface of one or more of a back brace, a lumbar support, a body sock, a knee brace, a leg brace, a wrist wrap, a wrist brace, a cervical brace, a hip brace, a split, an immobilizer, a cast, a foot brace, an ankle brace, or any other suitable orthosis device.

Various objects, features, aspects and advantages of the inventive subject matter will become more apparent from the following detailed description of preferred embodiments, along with the accompanying drawing FIGS. in which like numerals represent like components.

DETAILED DESCRIPTION

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Preferred systems of the inventive subject matter includes a pad coupled to at least one of (1) an inflatable member that provides an inward force to a part of a body of a wearer, and (2) at least one pod that can be placed relative to the inflatable member to concentrate, diffuse or otherwise direct the inward force provided by the inflatable member. Preferably the adjustable support is configured to couple with at least one panel of at least one brace such that the adjustable support is held in place at a desired position on a wearer's body.

Figure 1:
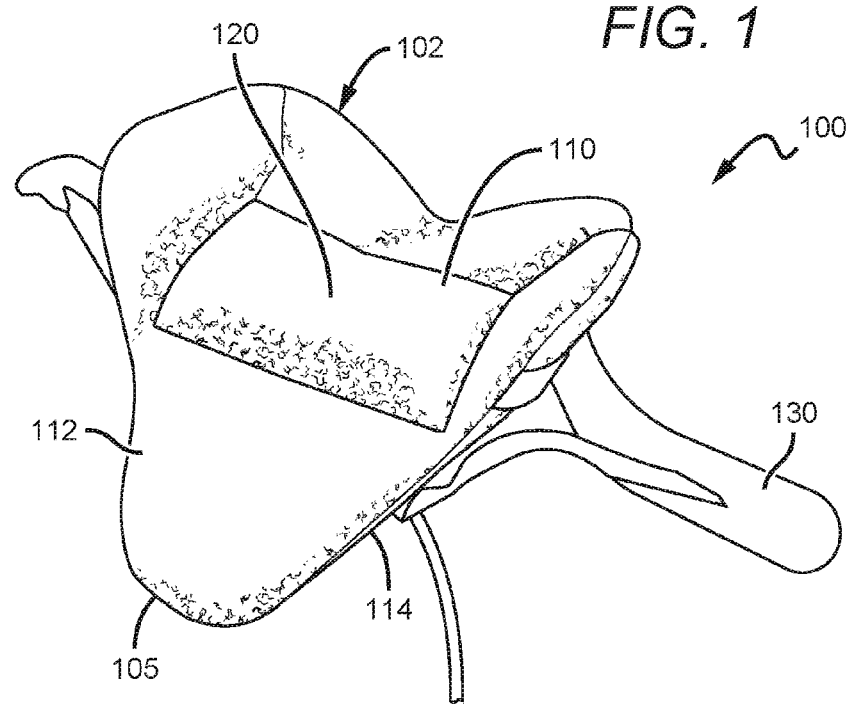
FIG. 1 is a perspective view of an adjustable support of the inventive subject matter.

FIG. 1 illustrates one contemplated embodiment of an adjustable support. Adjustable support 100 comprises an outer surface 114, an inner surface 112, a pad 102 having an outer material 105, and an inflatable member 110 disposed within the outer material 105. In other contemplated embodiments the inflatable member could be attached or coupled to pad 102 in any suitable manner. For example, the inflatable member could be disposed in a pocket of the pad, disposed within the pad or removably attached to the pad at one or more location via a fastener(s) (e.g., hook and loop, adhesive, button, snap, sewing, etc.).

Inflatable member 110 has an apex 120, which is the portion or point that has the greatest thickness when inflatable member 110 is fully inflated (e.g., the central point). Inflatable member 110 also includes at least a first fastener 130 that is sized and dimensioned to couple with a panel of at least one orthosis device. Where the adjustable support 100 can be movably coupled to a panel (as further described below), it is contemplated that the apex of the inflatable member can be adjustable relative to a central point of the panel. Additionally, where a pod is coupled to the adjustable support 100 (e.g., inserted into a pocket or other compartment of the adjustable support), an apex of the pod can be adjustable relative to the central point of the panel.

As used herein, the term "pod" should be interpreted broadly to include any insertable or removable item that modifies a force applied to a part of a wearer's body by an inflatable member. In some preferred embodiments, a pod can be contoured to the anatomy of a part of a wearer's body to which it can be applied.

Figure 2:
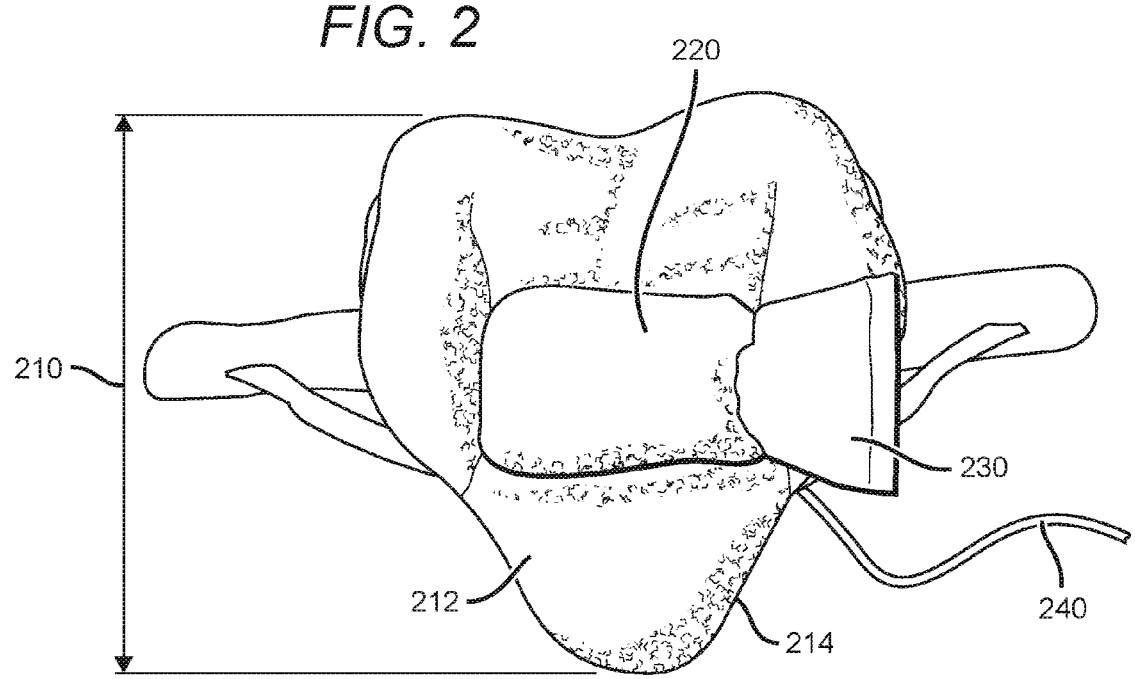
FIG. 2 is a view of an inner surface of an adjustable support including a pod.
Figure 3A:
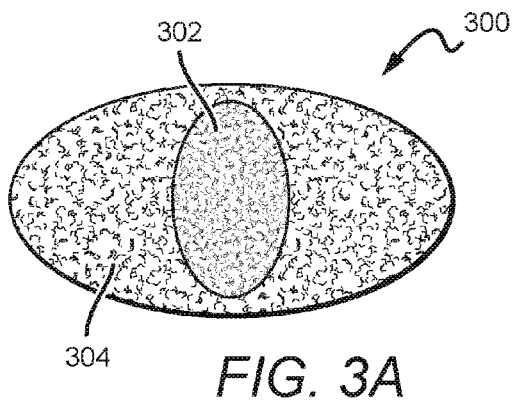
FIGS. 3A-3D illustrate some exemplary pods that could be removably inserted into an adjustable support.
Figure 3B:
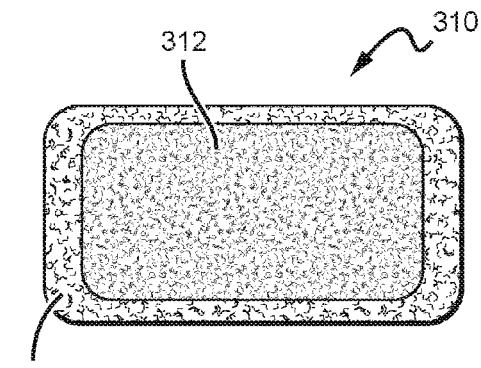
Figure 3C:
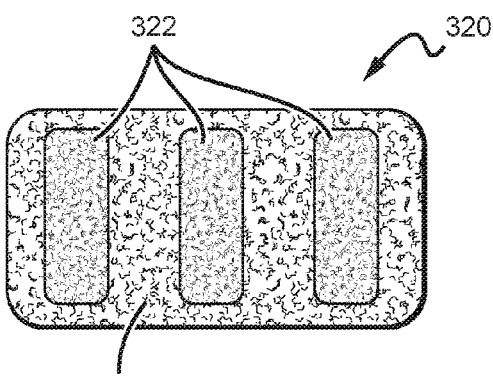
Figure 3D:
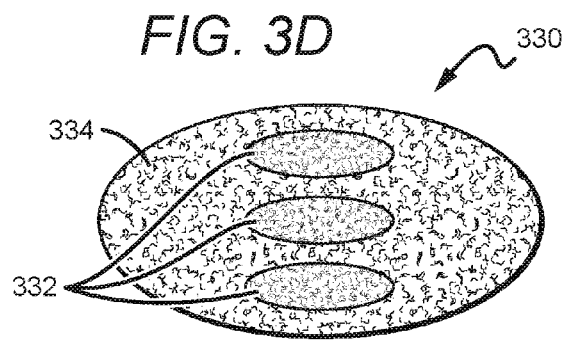

FIG. 2 illustrates an inner surface 212 of another embodiment of an adjustable support of the inventive subject matter, which includes a pod 230 in addition to an inflatable member (not shown). As used herein, an "inner surface" of an adjustable support is the surface of the support that would directly contact a wearer's body when correctly worn. Outer surface 214 is not shown but is the surface of the adjustable support that does not directly contact the neck of the wearer when worn. Pod 230 is disposed in a pocket 220 in the pad that overlies at least a portion of the inflatable member, and can be configured to diffuse, concentrate or otherwise adjust/direct an inward pressure that is applied to the wearer's body via the inflatable member. Where the adjustable support is coupled to a panel of an orthosis device, it is preferred that a vertical length of the pad 210 (e.g., the longest length of the pad, the midline of the pad, etc.) will be at least 0.5 inch, at least 1 inch, or even 1.5 or more inches greater than a vertical length of the panel (e.g., the longest length of the panel, the midline of the panel, etc.). This advantageously allows some vertical adjustment of the adjustable support relative to the panel (e.g., at least 0.5 inch, at least 1 inch, at least 1.5 inch, etc.) without exposing the wearer's skin to the panel.

Some contemplated pods include hot or cold packs that vary in size and shape and can be placed in a pocket of the pad in front of at least a portion of an inflatable member. Other contemplated pods include, for example, inflatable members of various shapes and sizes, and gel-filled members of various shapes and sizes. A pod's outer lining can be made of any suitable material(s), including for example, Nylon™, spandex, Lycra™, or plastic. While the examples described herein focus primarily on pods that are insertable and removable from a pocket of an adjustable support, it should be appreciated that the pods can be coupled with a pad in any suitable manner, including via hook and loop or other fasteners.

Additionally or alternatively, the pod can be filled with a gel, beads, pellets, polyurethane foam, or any other material(s) to any suitable fullness and with any suitable distribution to achieve the desired adjustment in inward pressure. Some exemplary pods are shown in FIGS. 3A-3D having various fillers distributed in various manners. Pod 300 has a rounded shape and includes a central and narrow (relative to the pod) tightly packed portion 302 and surrounding loosely packed portion 304. Pod 310 is more rectangular in shape, includes rounded edges, and has a larger tightly packed portion 312 that is similar in shape to the pod itself, and a surrounding loosely packed perimeter portion 314. Pod 320 includes a plurality of tightly packed portions 322 placed in a horizontal configuration, each tightly packed portion surrounded by a loosely packed portion 324. Pod 330 includes a plurality of tightly packed portions 332 placed in a vertical configuration, each tightly packed portion surrounded by a loosely packed portion 334.

In some aspects of the inventive subject matter, a pod can include a loosely packed portion (or a flatter portion) that is sized and dimensioned to overlie a bone of a wearer's body. The loosely packed portion can be partially or entirely bordered by tightly packed portions (or fuller / thicker portions) such that the pressure applied on the bone is minimized. In other aspects, where it is desirable to apply pressure to a bone, a tightly packed portion could be sized and dimensioned to overlie a bone of a wearer's body, and the tightly packed portion could be partially or entirely bordered by loosely packed portions. It should be appreciated that a single pod (e.g., pod 320) can achieve both of the above via an adjustment of the pod (or even the adjustable support) relative to at least one of the targeted portion of the wearer's body and a central point of a brace panel to which the adjustable support is coupled.

In some embodiments, especially where a tightly packed portion of a pod is larger than an inflatable member, the pod can diffuse an inward force that is applied via the inflatable member when a brace is worn. In some embodiments, especially where a tightly packed portion of a pod had a smaller surface area than an inflatable member, the pod can concentrate the inward force applied via the inflatable member when the brace is worn. It should be appreciated that a plurality of varying pods having different dimensions, fillers, materials, firmness, etc. can be insertable or removable from a pocket of some contemplated adjustable supports to allow a user to use different pods to achieve different results.

In some aspects of the inventive subject matter, an adjustable support of the inventive subject matter could be used to provide a pneumatic collar or other orthosis device. As one example, a pneumatic collar can include (1) a panel having a vertical length and outer and inner surfaces, and (2) a pad adjustably coupled to the panel via one or more fasteners. The pad can include or be coupled to an inflatable member in a manner that inflation of the inflatable member can increase an inward force applied to a neck of a user when the collar is worn.

The pad can advantageously have a vertical length that is at least 0.5 inch, at least 1 inch, or even 1.5 inches or more greater than the vertical length of the panel such that an adjustment of the pad relative to the panel in a vertical direction adjusts an apex of the inflatable member relative to the panel without exposing the user's neck to the inner surface of the panel. Additionally or alternatively, the pad can have a horizontal length that is at least 0.5 inch, at least 1 inch, or even 1.5 inches or more greater than the horizontal length of the panel such that an adjustment of the pad relative to the panel in a horizontal direction adjusts an apex of the inflatable member relative to the panel without contacting the user's neck with the inner surface of the panel.

Figure 4:
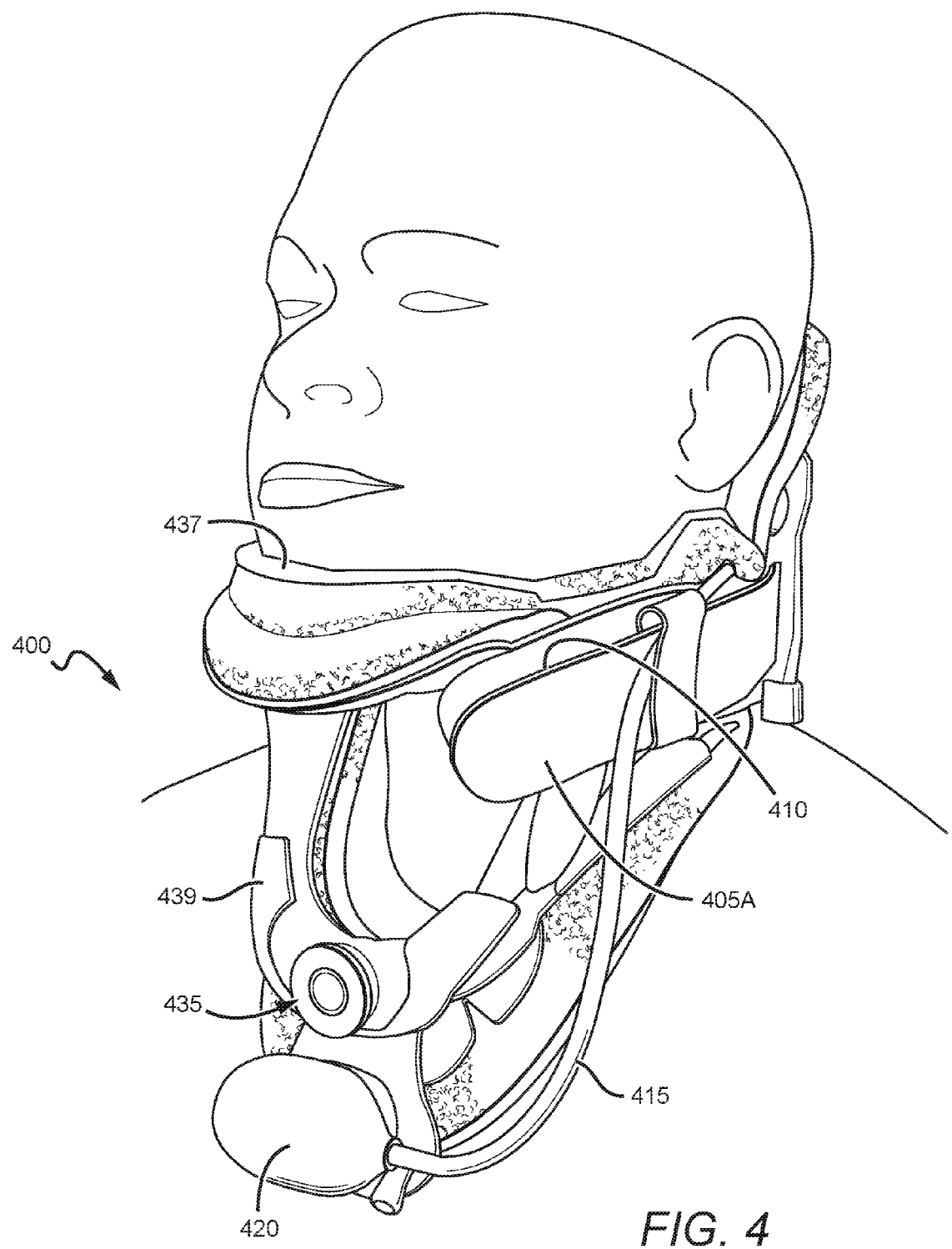
FIG. 4 is a side perspective view a pneumatic collar including an adjustable support of the inventive subject matter.

FIG. 4 illustrates an embodiment of a brace including an adjustable support of the inventive subject matter. First brace 400 is a pneumatic collar that includes an adjustable support (405 of FIG. 5). The adjustable support includes first fastener 405A, which can thread through an opening or slot included on or coupled to the first brace 400's panel and fasten with second fastener 410 of the same of different panel. Preferably, complementary fasteners are included on the opposite side of the adjustable support and first brace 400 such that the adjustable support can be secured to both left and right sides of the brace 400. In some contemplated embodiments, the adjustable support 405 can be used to couple the brace's rear panel with the brace's front panel. For example, the adjustable support could include a pad that removably attaches to the rear panel's inner surface, and a first fastener that threads through an opening of the rear panel and attaches to a fastener of the front panel's outer surface.

Tube 415 and pump 420 can be used by the wearer to inflate or deflate an inflatable member of adjustable support 405 to customize an inward pressure applied to the wearer's neck. The tube and pump can be attached to the inflatable member or can be removably coupled thereto. Additionally or alternatively, a housing or holder can be included in a panel of a brace to house or hold the pump when not in use. Brace 400 further includes a front panel portion having first adjustment mechanism 435 that allows a user to adjust a vertical position of a chin piece 437 relative to a collar body 439, which are coupled together via one or more pivot points or chin supports. An exemplary adjustment mechanism is a rack and pinion adjustment mechanism found in co-owned U.S. Pat. No. 7,674,234, wherein rotation of a pinion causes a rack to move a chin support member, which raises and lowers a chin piece.

Figure 5:
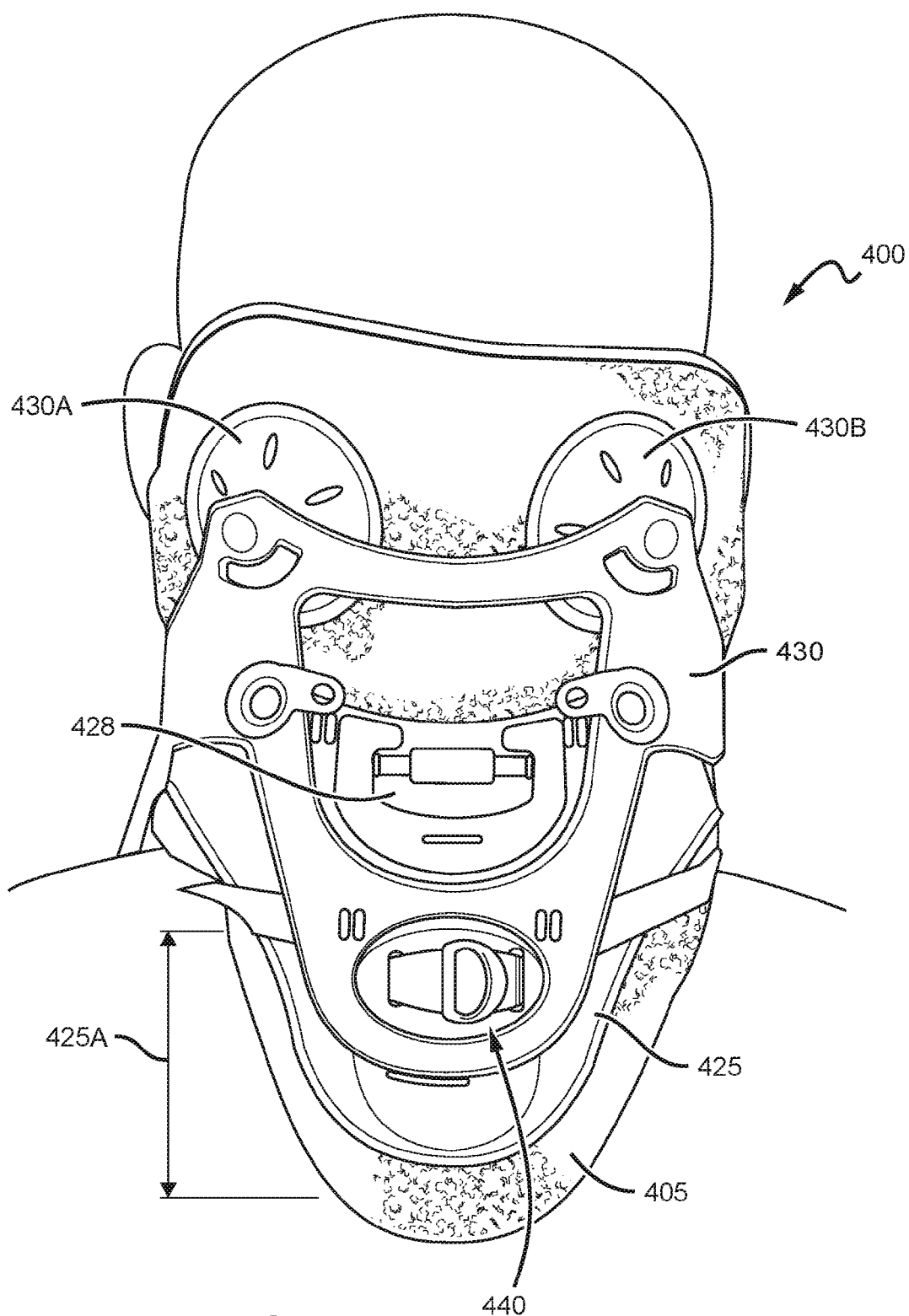
FIG. 5 is a rear view of the brace of FIG. 4.

FIG. 5 is a rear view of first brace 400 as worn by a wearer. The rear portion of brace 400 includes a lower panel 425 coupled to upper panel 430 via second adjustment mechanism 440. First adjustable support 405 is removably attached to lower panel 425's inner surface via one or more suitable fasteners (e.g., hook and loop fasteners, snaps, etc.) and has a vertical length that is greater than the first vertical length 425A of the lower panel 425. The oversized nature of the adjustable support relative to the panel allows a user to adjust an apex of the adjustable support's inflatable member without contacting the wearer's skin with the first panel's inner surface.

Adjustment mechanism 440 allows a user to adjust a vertical position of the upper panel 430 relative to the lower panel 425. Where an upper panel includes or is coupled with one or more occipital lobe supports (e.g., 430A, 430B as shown in FIG. 5), the adjustment mechanism 440 can further allow a user to adjust a vertical position of each of the occipital lobe supports 430A, 430B relative to the lower panel 425 with a single vertical adjustment. Brace 400 also includes a junction support 428 which can be configured to couple with a front or real portion of the brace. In the embodiment shown, junction support 428 couples to the rear portion of brace 400 and can comprise or couple with any suitable accessory, including for example, a belt, a back support, a strut, a chest supporting structure, or a realigning member.

It should be appreciated that any suitable adjustment mechanism 440 could be provided in a brace of the inventive subject matter, including the protrusion-notch-locking member adjustment mechanism shown in FIG. 5. Upper panel 430 includes a slidable locking member that includes or is otherwise coupled with a protrusion (not shown) sized and dimensioned to fit at least partially within some or all notches (not shown) of lower panel 425. Preferably, the protrusion is located on or against the inner surface of upper panel 430, the notches are located on an outer surface of lower panel 425 in a vertical orientation, and the locking member locks the protrusion at least partially within one of the notches. An exemplary rear portion and adjustment mechanism can be found in Applicant's co-owned U.S. Patent Application Publication No. 2013/0261519.

Figure 6:
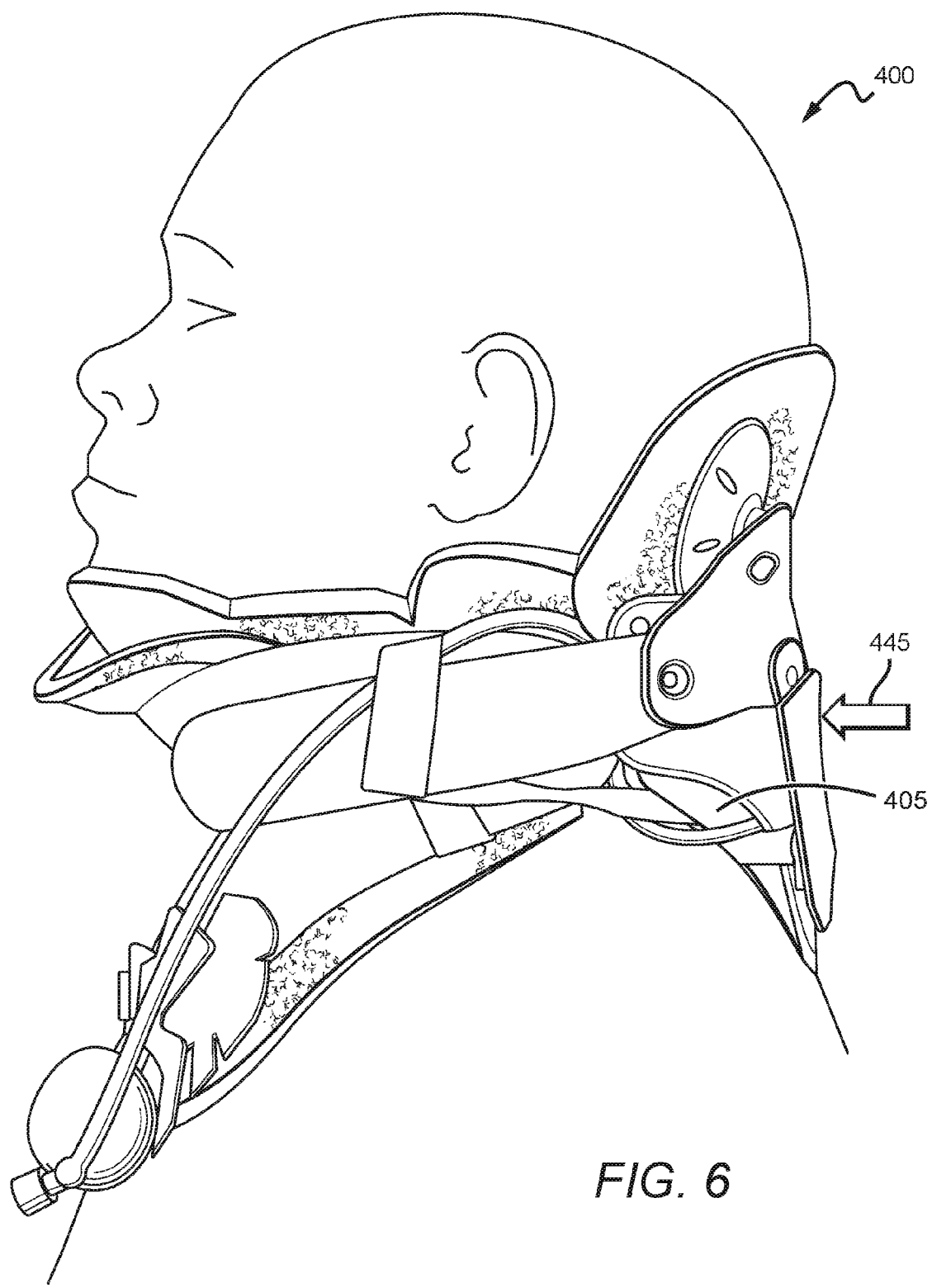
FIG. 6 is a side view of the brace of FIG. 4.

FIG. 6 is a side view of brace 400, which illustrates a force that can be applied to a wearer's body via the adjustable support 405. Where first adjustable support 405 is removably attached to an inner surface of a brace panel (as shown in FIG. 6 with respect to lower panel 425), inflation of the adjustable support's inflatable member will cause an inward force 445 to be applied to a portion of the wearer's body over which the inflatable member is placed. Where a pod is included to overlie at least a portion of an inflatable member, the pod can diffuse, concentrate, or otherwise direct the inward force 445 that is applied to the portion of the wearer's body based at least in part on the pod's size, shape, and the distribution of air or other filler within the pod.

It should be appreciated that while examples herein are generally directed towards pneumatic collars configured to apply an inward force to a neck of a wearer, an adjustable support of the inventive subject matter could be utilized with any suitable brace to provide adjustable support and force or pressure to any desired portion of a wearer's body. As some non-limiting examples, an adjustable support of the inventive subject matter could be sized and dimensioned to couple with one or more of a scoliosis brace, a cervical collar, a lumbar support brace, a knee brace, an ankle brace or wrap, a torso brace and a torso support. Viewed from another perspective, the adjustable support could be coupled to two or more braces and include an inflatable member to provide a force or pressure to one, some or all of a back, a neck, a lower back, a knee, an ankle, and a torso of a wearer. The adjustable support could couple with the braces via any suitable fasteners or attachment mechanisms, including for example, hook and loop fasteners, snaps, buttons, threading, or any other suitable means.

Additionally or alternatively, the adjustable support could include or couple with a pod that diffuses, concentrates or otherwise directs the force or pressure applied on the wearer via the inflatable member. Additionally or alternatively, the adjustable support could include or couple with a plurality of pods to direct the force or pressure in various ways.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A pneumatic collar for a wearer's neck, comprising:
   panel having an outer surface and an inner surface;
   an adjustable support removably coupled with an inner surface of the panel, the adjustable support including a pad and an inflatable member, wherein the inflatable member is configured to apply an inward force to a neck of the wearer; and
   wherein a position of the inflatable member relative to the panel is adjustable in a horizontal direction such that a position of the inward force is changed relative to the wearer's neck.

2. The collar of claim 1, wherein the adjustable support further includes a pod that directs the inward force that is applied to the neck of the wearer by the inflatable member.

3. The collar of claim 2, wherein the pod is sized and dimensioned to cooperate with the inflatable member to diffuse the inward force that is applied to the neck of the wearer.

4. The collar of claim 2, wherein the pod is sized and dimensioned to cooperate with the inflatable member to concentrate the inward force that is applied to the neck of the wearer.

5. The collar of claim 2, wherein the adjustable support comprises a pocket that is sized and dimensioned to receive at least one of the inflatable member and the pod.

6. The collar of claim 2, wherein the inflatable member is positioned between the pod and the panel.

7. The collar of claim 2, wherein the pod comprises a gel.

8. The collar of claim 1, wherein the inflatable member comprises a pump that is inflatable by the wearer, and wherein the position of the inflatable member is adjustable in the horizontal direction without exposing the wearer's neck to an inner surface of the panel.

9. The collar of claim 1, wherein the position of the inflatable member relative to the panel in the horizontal direction is adjustable up to 1 inch.

10. The collar of claim 1, wherein the panel comprises a first length, wherein the pad comprises a second length, wherein the first length of the panel overlies the second length of the pad, and wherein the second length is at least 0.5 inch greater than the first length.

11. The collar of claim 1, wherein the pad has a surface area greater than a surface area of the panel.

12. An adjustable support for a brace, comprising:
    a pad, an inflatable member and a pod;
    wherein the inflatable member is positioned entirely within a boundary of the pad, and is inflatable via a pump to provide an inward force to a portion of a wearer's body; and
    wherein the pod is positioned relative to the pad such that the inward force is concentrated or diffused on the portion of the wearer's body by the pod.

13. The system of claim 12, wherein the pad includes a first fastener that couples to a second fastener of a first brace to couple the pad to the first brace.

14. The system of claim 13, wherein the portion of the wearer's body comprises a neck.

15. The system of claim 13, wherein the portion of the wearer's body comprises a knee.

16. The system of claim 13, wherein the portion of the wearer's body comprises an ankle.

17. The system of claim 13, wherein the portion of the wearer's body comprises a back.

18. The system of claim 13, wherein the portion of the wearer's body comprises a torso.

19. The system of claim 12, wherein at least one of an apex of the inflatable member and an apex of the pod is adjustable relative to the pad.

20. The system of claim 12, wherein the adjustable support is sized and dimensioned to couple to at least two different braces configured to provide a force or pressure to different portions of the wearer's body.

* * * * *